Figure 3:
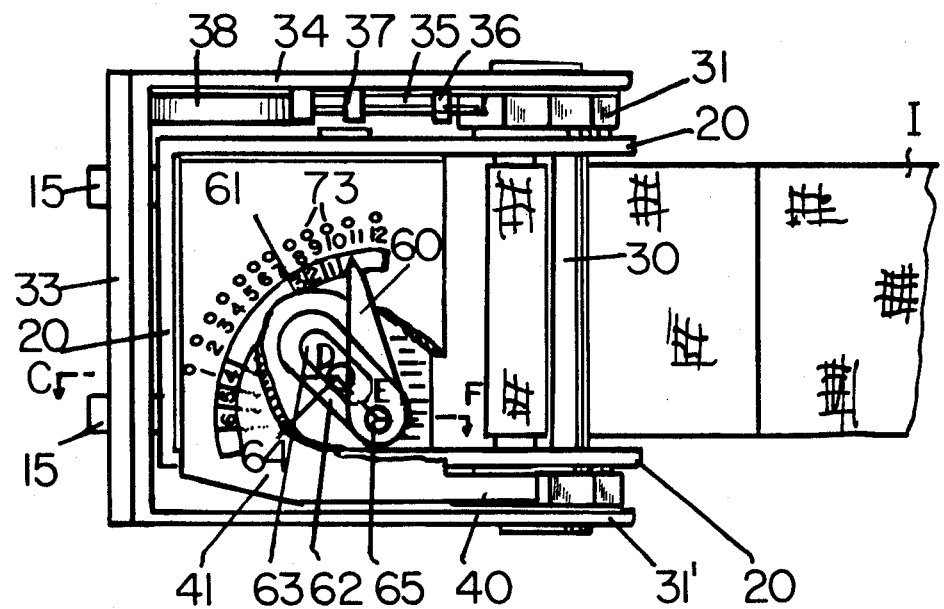

United States Patent [19]

Aginsky

[11] 4,243,039

[45] Jan. 6, 1981

[54] EMERGENCY TOURNIQUET

[76] Inventor: Yacov Aginsky, 18 Rachel St., Haifa, Israel

[21] Appl. No.: 48,086

[22] Filed: Jun. 13, 1979

[51] Int. Cl.³ ............................................ A61B 17/12
[52] U.S. Cl. ..................................................... 128/327
[58] Field of Search .................... 128/327, 686, 303 R

[56] References Cited

U.S. PATENT DOCUMENTS

| 1,279,784 | 9/1918 | Stopler et al. | 128/327 |
| 2,604,098 | 7/1952 | Kranc | 128/327 |
| 2,714,379 | 8/1955 | Raines | 128/686 |
| 3,095,873 | 7/1962 | Edmunds | 128/686 |
| 4,175,562 | 11/1979 | Honan | 128/303 R |

FOREIGN PATENT DOCUMENTS

| 818226 | 10/1951 | Fed. Rep. of Germany | 128/327 |
| 690293 | 4/1965 | Italy | 128/327 |
| 799 | 8/1915 | Netherlands | 128/327 |
| 209760 | 7/1940 | Switzerland | 128/327 |
| 8763 | of 1905 | United Kingdom | 128/327 |
| 291600 | 6/1928 | United Kingdom | 128/327 |

Primary Examiner—Lawrence W. Trapp
Attorney, Agent, or Firm—Schwartz, Jeffery, Schwaab, Mack, Blumenthal & Koch

[57] ABSTRACT

A tourniquet, destined to be used in an emergency, particularly on the battlefield, comprises a strap and a combined mechanism for tightening the strap and indicating the pressure exerted on the limb. The mechanism consists of a casing which contains a spool on which the free end of the strap is wound up by means of a pawl and ratchet mechanism. This casing is slidingly movable on a plate attached to the second end of the strap and urged in a direction opposed to the tightening force by two spiral springs positioned between the plate and the casing. Two tongues integral with the plate are made to protrude out of the casing by a length proportional to the compression of the springs and are marked to indicate the pressure exerted on the limb by the strap. These marks also give an indication of the maximum force allowable for an arm or a leg, taking into consideration the circumference of the respective limb.

10 Claims, 5 Drawing Figures

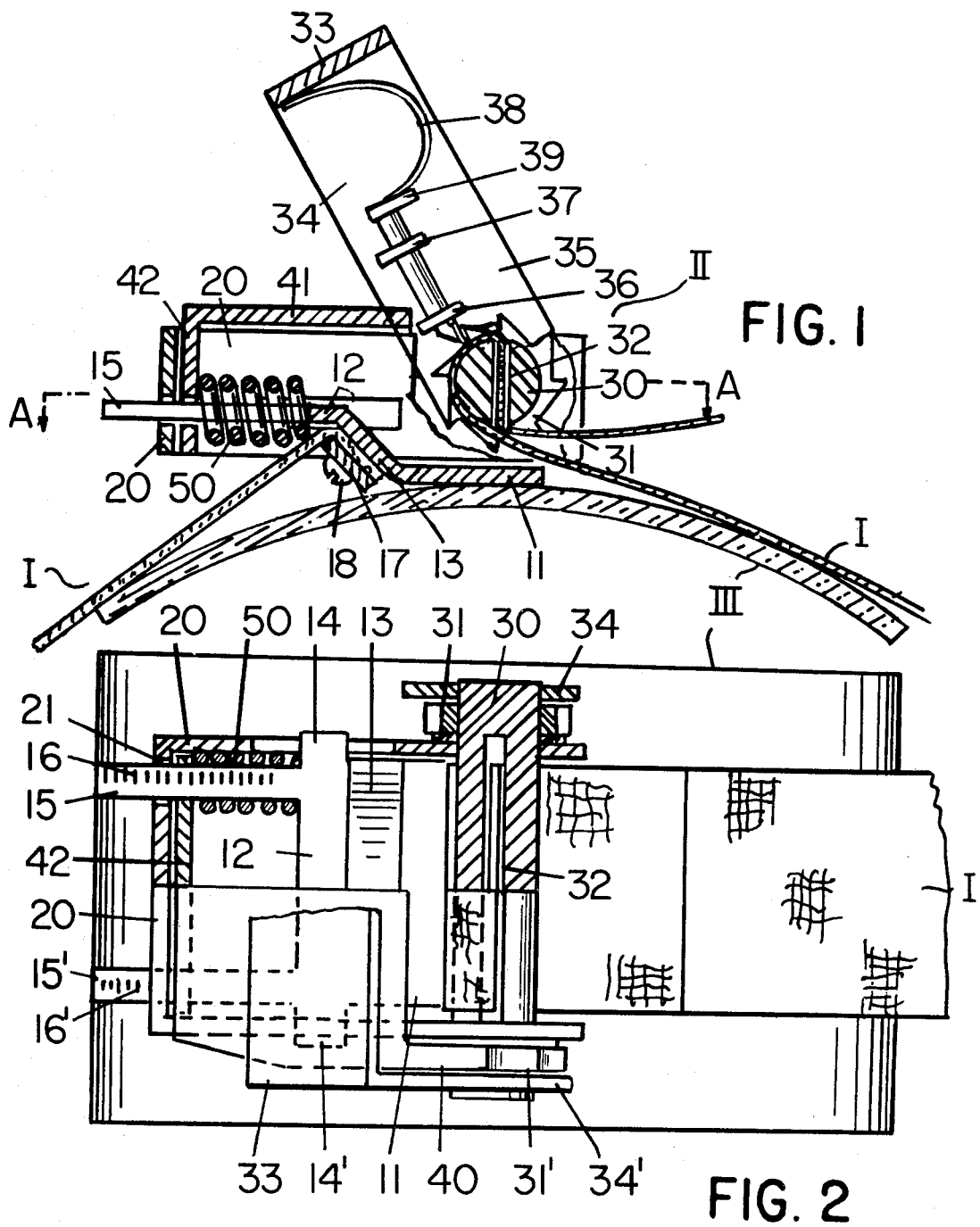

EMERGENCY TOURNIQUET

The invention relates to a tourniquet for controlling hemorrhage from an injured limb by pressure brought upon the blood vessel above the wounded part, more particularly to an emergency tourniquet to be used on the battle field. Conventional tourniquets consist of straps, cords, pads or rubber tubes tied around the limb at a pressure just sufficient to stop the blood flow, but not stronger in order to prevent damage to the tissue, nerves or blood vessels. It is also important to untie the tourniquet after a given time, otherwise gangrene is liable to set in, owing to the absence of blood circulation.

The mostly-used tourniquet consists of a rubber hose tied around the injured limb and inflated by means of a rubber bellow to the required pressure which is indicated on an attached pressure gauge. This kind is suitable for hospitals or clinics, where the equipment can be well tended and preserved; it is, however, not suitable for emergency treatment to be carried out by unskilled or semiskilled personnel which happen to be present on the site of fires, road accidents and particularly on the battle field.

Besides the fact that rubber hoses and rubber bellows would deteriorate while stored in army installations for longer periods, carrying of three items, i.e. the rubber hose, the bellow and the pressure gauge and their assembly on the spot is an encumbrance for the medic or the corpsman in the field, where every second counts to save the life of a soldier.

It is furthermore important to mark on the tourniquet the exact time at which it was applied, to enable personnel behind the front to carry out an operation in good time and to release the tourniquet before permanent damage is done to the limb. If such information is readily available it will enable the surgeon in charge to determine the sequence of operations of different soldiers brought back from the front.

In view of the foregoing it is the object of the present invention to provide a tourniquet which will not deteriorate with time. Another object is to provide the tourniquet with clearly distinguishable marking indicating the pressure to which the tourniquet may be tightened and the actual pressure applied to the specific limb, be it an arm or a leg. Still another object is to provide simple time indicating means on the tourniquet body proper to be set to the exact hour and fraction thereof by the person applying the apparatus.

The tourniquet, according to the invention, comprises a strap, a strap-tightening mechanism and a pressure-indicating device integral with the tightening mechanism. Herein the tightening mechanism consists of a rigid front part firmly and permanently attached to the front end of said strap, and a rigid rear portion carrying near its rear end a slotted spool which latter is adapted to be unidirectionally rotated by a pawl and ratchet mechanism and, by this rotation, to wind up the rear end of said strap wound around the limb, to shorten and tighten said strap around said limb and thereby exerting circumferential pressure on said limb, said front portion and said rear portion being slidingly connected and pressed towards each other by at least one compression spring so dimensioned as to permit a rearward movement of the rear portion relative to the front portion proportionally to the pull exerted by the tightened strap. And herein the pressure indicating device is in the form of a scale combined with pointer means indicating on said scale the pull of said strap end, said scale being provided with marks indicating the permissible pull, related to the circumferential pressure to be exerted on an arm and a leg respectively for at least two different diameters of an arm and a leg respectively.

In a preferred embodiment the relative movement of the two parts is transmitted by means of a lever to a hand moving across a dial, thus magnifying the indication of the movement to readily readable dimensions. This dial is preferably marked in a bold manner to indicate the permissible force to be applied to a leg or an arm, also taking into account the thickness of the respective limb, in addition, special marking may be provided on the strap which correspond to the markings on the dial, permitting even a completely unskilled person to tighten the tourniquet correctly.

An additional feature is a pointer manually movable across the same or another dial which is provided with a scale showing the twelve hours of a day; this hand can be positioned on the hour at which the tourniquet was applied. A still more accurate information can be supplied by providing a sliding or turning pointer showing the quarter hours as well.

Figure 4:
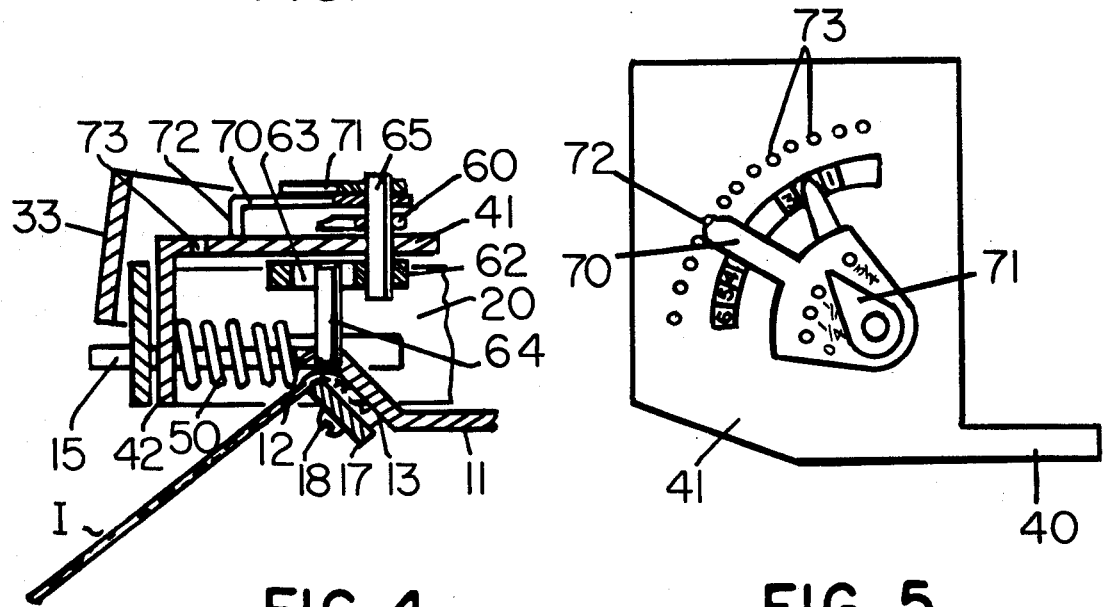
Figure 5:
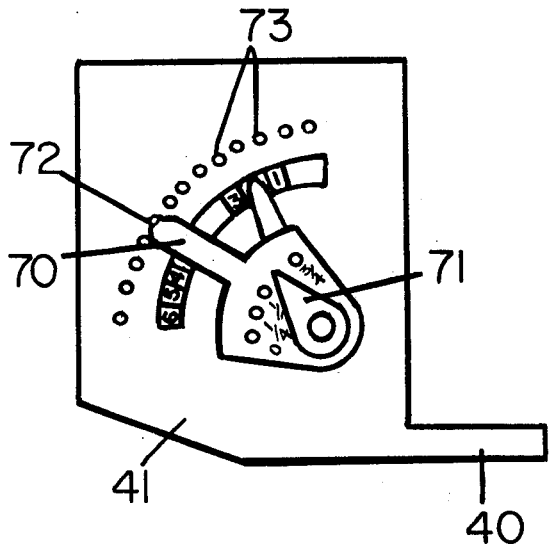

In the accompanying drawings which illustrate, by way of example, two embodiments of the invention, FIG. 1 is a longitudinal section through a tourniquet comprising a pressure-indicating device, FIG. 2 shows, in its upper half, a section along A—A of FIG. 1, and in its lower half a plan view of the tourniquet of FIG. 1, FIG. 3 is a plan view of the tourniquet as illustrated in FIG. 1, however provided with another kind of pressure indicating device, FIG. 4 is a section along C-D-E-F of FIG. 3, and FIG. 5 is a plan view of the cover plate of the tourniquet as illustrated in FIG. 3, provided with an additional time marking device.

With reference to FIG. 1, 2 and 3 of the drawings a tourniquet comprises a strap I, a tightening mechanism II and a curved protection shield III to which the mechanism is firmly attached. The mechanism comprises a front portion constructed of a metal sheet bent to form a base 11 connected to the shield III and an offset guide plate 12, the two being connected by a sloping portion 13. The guide plate is provided on both sides with sideways protruding lugs 14, 14', and is cut out in its front portion to form two strip-shaped, forwardly protruding tongues 15, 15' which are, on their upper surfaces provided with a scale 16, 16' each. The front end of the strap I is firmly attached, and clamped to the sloping portion 13 by a plate 17 and screws 18.

The rear portion comprises a U-shaped main body 20 which serves as support for a spool 30 adapted to be rotated by a pawl-and-ratchet mechanism. The main body 20 is perforated in its web or front portion by two slots 21 through which protrude the tongues 15, 15' of the guide plate, and is further perforated on its both sides by longitudinal slots 22, serving as guides for the protruding lugs 14 of the guide plate 12. By means of these slots 22 the main body is longitudinally slidable in relation to the front portion which latter is fixed to the shield, but it is prevented from tilting or moving in any other direction by the tongues 15 guided in the slots 21. The rear portion and the front portion are drawn together by two spiral springs 50 threaded on the tongues 15, 15' which press the rear portion to the front relative to the front portion and the shield.

A longitudinally slotted spool 30 is rotatably fastened in the rear portion of the main body 20 and held in axial position by two ratchet wheels 31, 31' each rigidly fastened to one end of the spool. The slot 32 in the spool serves to accommodate the rear end of the strap I which can be pulled through this slot by hand in order to tie it initially loosely around the injured limb, before the strap is being tightened by rotation of the spool.

The spool is rotated by a driving mechanism which comprises a U-shaped driving arm consisting of a web 33 and two legs 34, 34', this arm is rotatable about the spool and is mounted on the outer ends of this spool in loosely fitting bores provided at the ends of the legs 34, 34'. One of the legs, in the present case leg 34, is provided with a driving pawl 35 which is axially guided in two inwardly protruding, perforated lugs 36, 37 fastened to the inside of the leg 34. The rear end of the pawl 35 is enlarged to form a plate 39 to which one end of a leaf spring 38 is connected, the other end of this spring being attached to the inside of the web 33 of the driving arm. The pawl engages with a tooth of the ratchet wheel, and clockwise rotary movement of the driving arm, in rearward direction, serves to rotate the spool in the same direction, thereby winding the strap on the spool and tightening it around the limb.

A holding pawl 40 prevents the return of the spool after the driving pawl is released upon anticlockwise rotation of the driving arm. This holding pawl forms part of an angular cover plate 41 one angle-side of which covers the top of the main body and is elongated on its outer rear end, on the side opposite the driving pawl, to form a rearwardly extending tongue engaging with the ratchet wheel 31'. The other angle side 42 of the cover plate is positioned inside of the web of the main body and biased against the latter by the two aforedescribed springs 50. This angle side is provided with slots similar and co-axial with the slots 21 in the main body, the two tongues 15, 15' protruding through these as well. In order to disengage the holding pawl from the ratchet, the cover plate 41 can be slightly lifted by hand against the pressure of the springs 50, and the spool is then free to return, provided the driving pawl is similarly withdrawn out of engagement with a tooth of the ratchet wheel 30, by pulling it back against the action of the spring 38. A catch is preferably provided on the driving arm, keeping the driving pawl in withdrawn position; this catch is not shown as it may be of any known design.

The scales 16, 16'—or at least one of these—are marked to indicate the relative position of the rear portion in relation to the front portion according to the pull exerted by the strap. These marks should distinctly indicate the pull necessary to stop blood flow in a thin, normal or thick arm and in a thin, normal or thick leg; thus the first mark appearing on the tongue 15 protruding out of the front portion of the main body 20 will be the mark for a thin arm, as of a child, while the last mark appearing, after the springs are fully compressed, will be in respect of a fat leg. It is understood that the pull should not exceed beyond these marks in order not to endanger the limb.

The embodiment of FIG. 3 illustrates a pressure-indicating device wherein the relative displacement of the front and rear portion of the tightening mechanism is transmitted to a hand 60 moving across a scale 61 in quadrant shape, provided on top of the cover plate 41 of the rear portion. The hand 60 is rigidly fastened to the upper portion of a vertical shaft 65 which is rotatable in a bore in the cover plate 41, while a slotted lever 62 is rigidly fastened to the lower portion of the shaft underneath the cover plate. The slot 63 in the lever 62 is in permanent engagement with a vertical pin 64 fastened in the guide plate 12 of the front portion of the mechanism. As the pull of the strap I increases, the horizontal distance between the two portions increases proportionally, and likewise the distance between the shaft 65 and the pin 64. This movement causes the slotted lever to rotate together with the shaft 65 and the hand 60, which latter moves across the scale 61. The scale is marked to include two separated areas, each containing three fields, 1,2,3 and 4,5,6, respectively. These fields are preferably coloured in different shades which correspond to areas on the strap dyed in the same sequence. These coloured areas serve to make the application of the tourniquet easily understood by a layman after having received a short explanation. The permissible pressure on the circumference is $P_1 = 300$–$359$ mm Hg for an arm and $P_2 = 450$–$500$ mm Hg for a leg. The force or pull acting on the two ends of the strap is, therefore, $F = p.L$, wherein L equals the circumference of the arm or leg. Returning to the coloured areas on the scale and on the strap, the field 1 would indicate the permissible pressure not to be exceeded on a thin arm, say of a child, while the other extreme, field 6, would indicate the pressure necessary to close the blood vessels in a fat leg. The strap will be similarly coloured, the specific coloured area appearing adjacent the spool corresponding to the circumference of the enclosed limb. This colouring will enable the person applying the tourniquet to tighten the strap until the hand points to the colour on the dial corresponding to the colour on the strap, thus resulting in a sufficiently exact circumferential pressure.

An additional device for marking the hour and fractions thereof is mounted on the shaft 65, in the form of two pointers 70 and 71, loosely rotatable on said shaft, which are shown in FIGS. 4 (top) and 5. The pointer 70—which is resilient—is provided at its outer end with a downwardly extending pin 72 which is adapted to engage with any of twelve holes 73 arranged on a quadrant which are marked 1 to 12 to indicate the hour at which the tourniquet was applied. A second pointer 71 is mounted on top of the first pointer which latter has four marks, 0, $\frac{1}{4}$, $\frac{1}{2}$, and $\frac{3}{4}$, indicating the quarter hours. The person, after having fixed and tightened the tourniquet, positions the two pointers to the hour and fraction thereof, so as to permit loosening of the tourniquet before permanent damage can occur to the limb.

I claim:

1. An emergency tourniquet for controlling hemorrhage from a limb such as an arm or a leg, comprising a strap, a strap-tightening mechanism and a pressure-indicating device integral with the tightening mechanism, wherein said tightening mechanism consists of a rigid front part firmly and permanently attached to the front end of said strap, and a rigid rear portion carrying near its rear end a slotted spool which latter is adapted to be unidirectionally rotated by a pawl and ratchet mechanism and, by this rotation, to wind up the rear end of said strap wound around the limb, to shorten and tighten said strip around said limb and thereby exerting circumferential pressure on said limb, said front portion and said rear portion being slidingly connected and pressed towards each other by at least one compression spring so dimensioned as to permit a rearward movement of the rear portion relative to the front portion proportionally to the pull exerted by the tightened strap, said pressure indicating device being in the form of a scale combined with pointer means indicating on said scale the pull of said strap end, said scale being provided with marks indicating the permissible pull, related to the circumferential pressure to be exerted on an arm and a leg respectively for at least two different diameters of an arm and a leg respectively.

2. An emergency tourniquet as defined in claim 1 wherein the front part is firmly connected to a curved protection shield adapted to be laid close to the skin of the limb.

3. An emergency tourniquet as defined in claim 1 wherein said front portion is provided with at least one forwardly extending tonque the upper surface of which is provided with a scale, said tongue and said scale being positioned in relation to said rear portion in a manner so as to protrude beyond the said rear portion by a length corresponding to the rearward movement of said rear portion due to the pull of said strap end.

4. An emergency tourniquet as defined in claim 1 wherein said slotted spool in said rear portion is provided at both ends with one ratchet wheel each firmly connected thereto.

5. An emergency tourniquet as defined in claim 4 wherein a driving arm is rotatable about said spool and provided with a driving pawl adapted to engage with the teeth of one of the ratchet wheels and to rotate the spool.

6. An emergency tourniquet as defined in claim 4 wherein said rear portion is provided with an angular cover plate which is rearwardly extended to form a holding pawl adapted to engage with the teeth of the second ratchet wheel not engaging with the driving pawl.

7. An emergency tourniquet as defined in claim 6 wherein said cover plate is biased into engagement with said ratchet wheel by means of said compression spring which latter serves to hold the rear portion pressed toward the front portion.

8. An emergency tourniquet as defined in claim 6 comprising a pressure indicating device consisting of a scale in the form of a quadrant provided on the top surface of said cover plate, a shaft rotatably fixed in said cover plate in the center of said quadrant, a hand movable across said scale firmly attached to the top of said shaft, a slotted lever firmly attached to the bottom end of said shaft, and a pin engaging with a radial slot in said lever and rigidly fastened in said front portion, the several parts of the pressure indicating device being so dimensioned and so positioned that the rearward motion of the rear portion proportional to the pull exerted by the strap, is indicated by said hand on said scale, which latter is marked to indicate the permissible pull for various sizes of an arm and a leg, respectively.

9. An emergency tourniquet as defined in claim 8 wherein a quadrant of twelve holes is provided in said cover plate concentric with said scale of the pressure indicating device, and wherein a first pointer is rotatably mounted on the upwardly extended end of said rotatable shaft, said first pointer being provided with a downwardly extending pin adapted to be manually engaged with each one of said twelve holes which are numbered 1 to 12 to indicate the hour of application of the tourniquet.

10. An emergency tourniquet as defined in claim 9 wherein said first pointer is of sufficient width to accommodate on its upper surface four spaced-apart marks equidistant from said shaft which are numbered to indicate the quarters of the hour, and wherein a second pointer is rotatably mounted on said shaft, above the first pointer, adapted to be manually positioned opposite one of the four marks.

* * * * *